United States Patent [19]

Lentz et al.

[11] Patent Number: 4,847,429

[45] Date of Patent: Jul. 11, 1989

[54] SYNTHESIS OF PHENYLHYDROQUINONES

[75] Inventors: Carl M. Lentz; Bruce L. Gustafson; Dale E. Van Sickle; Joseph S. Bowers, Jr., all of Kingsport, Tenn.

[73] Assignee: Eastman Kodak Company, Rochester, N.Y.

[21] Appl. No.: 81,209

[22] Filed: Aug. 3, 1987

[51] Int. Cl.$^4$ .............................................. C07C 43/02
[52] U.S. Cl. ................. 268/643; 260/396 R; 568/657; 568/771; 568/772
[58] Field of Search ............... 568/643, 557, 771, 772, 568/628; 260/396 K

[56] References Cited

U.S. PATENT DOCUMENTS

| | | | |
|---|---|---|---|
| 2,090,173 | 8/1934 | Zahn et al. | 568/643 |
| 2,704,773 | 3/1955 | Young et al. | 260/620 |
| 2,831,898 | 4/1958 | Ecke et al. | 260/624 |
| 3,426,358 | 2/1969 | Schlichting et al. | 260/621 |
| 3,580,970 | 5/1971 | Swift | 260/621 H |
| 3,898,289 | 8/1975 | Schneider | 260/621 H |
| 3,900,522 | 8/1975 | Greco | 260/621 H |
| 3,919,333 | 11/1975 | Wollensak | 260/624 R |
| 3,953,529 | 4/1976 | Yonemitsu et al. | 260/621 R |
| 3,987,112 | 10/1976 | Lyons | 260/621 H |
| 4,002,693 | 1/1977 | King et al. | 260/620 |
| 4,016,211 | 4/1977 | Fattori et al. | 260/611.5 |
| 4,024,195 | 5/1977 | Yonemitsu et al. | 260/621 R |
| 4,024,196 | 5/1977 | Krekeler et al. | 260/621 H |
| 4,035,428 | 7/1977 | Fishel et al. | 260/620 |
| 4,041,085 | 8/1977 | Frabetti, Jr. | 260/621 R |
| 4,060,559 | 11/1977 | Goto et al. | 260/620 |
| 4,080,390 | 3/1978 | Imamura | 260/620 |
| 4,085,150 | 4/1978 | Smith | 260/621 R |
| 4,088,702 | 5/1978 | Goto et al. | 568/747 |
| 4,160,113 | 7/1979 | Müller et al. | 568/772 |
| 4,319,054 | 3/1982 | Maki et al. | 568/772 |
| 4,415,477 | 11/1983 | Rozovsky et al. | 502/178 |
| 4,417,076 | 11/1983 | Rozovsky et al. | 568/361 |
| 4,538,009 | 8/1985 | Goetz et al. | 568/772 |

OTHER PUBLICATIONS

Brassard et al., "L'arylation des Quinones par les Sels de Diazonium, 1. Sur. la Synthesis des Monoayl-p-Benzoquinones," Canadian Journal of Chemistry, vol. 36, pp. 700–708 (1958).

Thomas, "Synthesis of 2,5-Diaryl-1,4-Benzoquinones," Journal of the Chemical Society, pp. 2269–2270 (1964).

Itahara, "Oxidative Coupling of Quinones and Aromatic Compounds by Palladium (II) Acetate," in Journal of Organic Chemistry, vol. 50, pp. 5546–5550 (1985).

74 JACS, pp. 1327–1329 (1952), Barnes et al., "1-(2',-3'-Dimethoxyphenyl)-1-Cyclohexene-6-one".

Chemical Abstr., vol. 45, p. 125 (1951), Bergmann et al., "2-(2,3-Dimethyoxyphenyl)-Cyclohexene".

Primary Examiner—Glennon H. Hollrah
Assistant Examiner—Raymond Covington
Attorney, Agent, or Firm—S. E. Reiter; William P. Heath, Jr.

[57] ABSTRACT

Process is disclosed for the preparation of phenylhydroquinones by the alkylation of hydroquinone (or derivatives thereof) with the cyclohexyl moieties, cyclohexanol or cyclohexene (or derivatives thereof), followed by dehydrogenation of the intermediate cyclohexylhydroquinone.

26 Claims, No Drawings

SYNTHESIS OF PHENYLHYDROQUINONES

This invention relates to synthetic methods for the preparation of phenylhydroquinone and derivatives thereof.

BACKGROUND OF THE INVENTION

Phenylhydroquinone is a useful monomer for the preparation of liquid crystal polyesters and speciality resins. The availability of a variety of phenylhydroquinone derivatives would be of interest, for example, for the preparation of new liquid crystal polyesters and specialty resins having a range of properties not possessed by known materials.

Prior art preparative methods are limited in their ability to produce substituted phenyl hydroquinone products, involve the use of expensive chemicals as starting materials and employ exotic chemical conversions. For example, phenylhydroquinone has been prepared by reaction of the diazonium salt of aniline with parabenzoquinone, followed by catalytic reduction of the intermediate product, phenylparabenzoquinone, to produce phenylhydroquinone.

An alternate method reported in the literature for the preparation of phenylparabenzoquinone involves the reaction of benzene with parabenzoquinone in the presence of equimolar amounts of palladium acetate. This process only gives low yields of the desired intermediate, phenylparabenzoquinone, and is also quite expensive because large amounts (equimolar quantities) of the palladium acetate promoter are required.

There is, therefore, a need for high yield, reduced cost synthetic methods for the preparation of phenylhydroquinone, and derivatives thereof.

OBJECTS OF THE INVENTION

An object of the present invention, therefore, is an efficient process for the preparation of phenylhydroquinone employing readily available and relatively inexpensive starting materials.

Another object of the present invention is an efficient process for the preparation of substituted phenylhydroquinones.

These and other objects of the invention will become apparent from inspection of the detailed description and appended claims which follow.

STATEMENT OF THE INVENTION

In accordance with the present invention, we have discovered that phenylhydroquinone and derivatives thereof can be readily prepared by first alkylation of hydroquinone (or derivatives thereof) with a cyclohexyl moiety, then dehydrogenation of the resulting intermediate, cyclohexylhydroquinone, under dehydrogenation conditions such that hydrogenolysis of the hydroquinone hydroxy groups is minimized.

The invention process uses relatively inexpensive and readily available starting materials, employs readily available catalytic materials and provides high yields of the desired phenylhydroquinone products.

DETAILED DESCRIPTION OF THE INVENTION

In accordance with the present invention, there is provided a process for the preparation of phenylhydroquinone derivatives of the structure

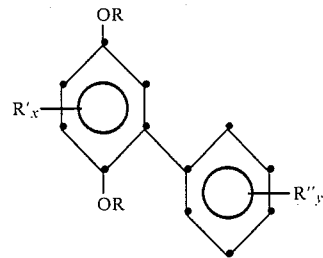

wherein
each R is independently H, a $C_1$–$C_{20}$ alkyl or substituted alkyl radical;

wherein Y is a $C_1$–$C_{20}$ alkyl or substituted alklyl radical; or a $C_6$–$C_{12}$ aryl, alkyl substituted aryl or substituted aryl radical;

each R' is independently a $C_1$–$C_{20}$ alkyl or substituted alkyl radical; $C_5$–$C_{12}$ cycloalkyl or substituted cycloalkyl radical;

wherein Y is a $C_1$–$C_{20}$ alkyl or substituted alkyl radical; or a $C_6$–$C_{12}$ aryl or substituted aryl radical;

R" is the same as R', and each R" is selected independently of R' and independently of one another;

wherein the substituents, when present on R, R' or R" are selected from the group consisting of:
—OR, wherein R is as defined above;
—$NO_2$;
—X, wherein X is a halide;

wherein R is as defined above;

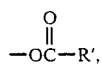

wherein R' is as defined above; and
—$SO_zR$, wherein z is an integer which varies in the range of 0 up to 3 and R is as defined above;
wherein x is a whole number in the range of 0 up to 3; and
wherein y is a whole number in the range of 0 up to 5;
said process comprising:
(1) contacting a hydroquinone compound of the structure:

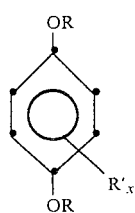

with a cyclic compound of the structure:

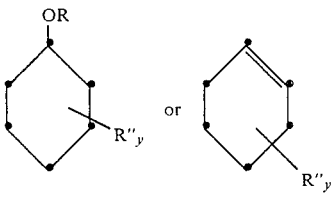

in the presence of an acid under alkylation conditions suitable to produce a cyclohexylhydroquinone or derivative thereof having the structure:

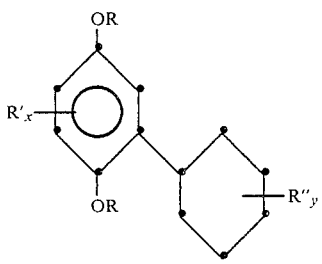

and thereafter (2) subjecting said cyclohexylhydroquinone or derivative thereof to dehydrogenation conditions which minimize the occurrence of hydrogenolysis.

The starting materials employed in the practice of the present invention are hydroquinones of the structure:

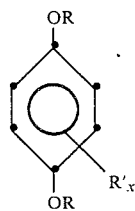

and cyclohexyl moieties of the structure:

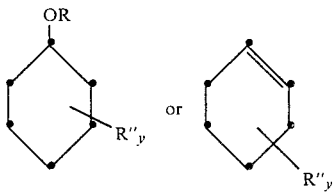

Hydroquinone compounds which satisfy the above formula include hydroquinone, methylhydroquinone, chlorohydroquinone, isopropylhydroquinone, t-butylhydroquinone, 2-t-butyl-4-methoxyphenol, butylhydroquinone, octylhydroquinone, dodecylhydroquinone, octadecylhydroquinone, butanoylhydroquinone, octanoylhydroquinone, dodecanoylhydroquinone, and octadecanoylhydroquinone.

Cyclohexyl compounds which satisfy the above formulae include cyclohexanol, cyclohexene, alkyl cyclohexanols, such as, for example, 2-methyl cyclohexanol and 4-methyl cyclohexanol; aryl cyclohexanols, such as, for example, 2-phenyl cyclohexanol and 4-phenyl cyclohexanol; alkoxy cyclohexanols, such as, for example, 2-methoxy cyclohexanol and 4-methoxy cyclohexanol; acyl cyclohexanols, such as, for example, 2-acetoxy cyclohexanol and 4-acetoxy cyclohexanol; alkyl cyclohexenes, such as, for example, 2-methyl cyclohexene and 4-methyl cyclohexene; aryl cyclohexenes, such as, for example, 2-phenyl cyclohexene and 4-phenyl cyclohexene; alkoxy cyclohexenes, such as, for example, 2-methoxy cyclohexene and 4-methoxy cyclohexene; acyl cyclohexenes, such as, for example, 2-acetoxy cyclohexene and 4-acetoxy cyclohexene; and the like.

The alkylation of hydroquinones with cyclohexyl moieties in accordance with the present invention is carried out in the presence of acid catalyst. Those of skill in the art can readily identify numerous acids which are suitable for such purpose. By way of example, acids such as the following are useful:
phosphoric acid,
sulfuric acid,
methanesulfonic acid,
trifluoromethanesulfonic acid,
polyphosphoric acid,
acidic molecular sieves,
$SiO_2/Al_2O_3$,
p-toluenesulfonic acid,
trichloroacetic acid,
dichloroacetic acid,
trifluoroacetic acid,
aluminum trichloride,
aluminum tribromide,
boron trifluoride, and
acidic polymeric resins, such as, for example, Amberlyst 15, and Aerocat.

Preferred for ease of handling, workup, etc., are the acidic polymeric resins such as, for example, Amberlyst 15 and Aerocat.

Reaction conditions employed for the alkylation step can vary within wide ranges. The alkylation reaction can, therefore, be carried out over a wide range of temperatures, reaction times, and the like. Generally employed are reaction temperatures in the range of about 0° up to 200° C., with reaction pressures in the range of about 0.01 up to 10 atmospheres, and contact times in the range of about 0.01 up to 30 hours.

Preferred reaction conditions for the alkylation step will vary as a function of the starting materials employed, the acid catalyst used, the catalyst/substrate ratio, desired conversion levels, and the like. Those of skill in the art can readily determine preferred reaction conditions. Thus, for example, with cyclohexanol as one of the starting materials, preferred reaction temperature falls within the range of 100° up to 150° C. When cyclohexene is employed as one of the starting materials, preferred reaction temperature falls within the range of 75° up to 95° C.

The substrate to acid weight ratio can vary within wide ranges. When solid acid catalysts are used, it is preferred to employ relatively high substrate/acid weight ratios, on the order to 5:1 up to 20:1. Conversely, when soluble acid catalysts are used, it is preferred to employ lower substrate/acid ratios, on the order of 1:4 up to 2:1. In all cases, it is desirable to use at least an equimolar amount of the hydroquinone moiety relative to the cyclohexyl moiety. Preferably, hydroquinone/cyclohexyl molar ratios will fall in the range of 1:1 up to 10:1. Most preferably, at least a 30% molar excess of the hydroquinone moiety will be employed, thereby minimizing the formation of polyalkylated hydroquinone derivatives.

The use of solvent in the alkylation step is optional. When employed, suitable solvents are those which are stable under reaction conditions. Examples of suitable solvents are water, water/acid mixtures, excess hydroquinone, excess soluble acid catalyst, benzene, toluene, mesitylene, biphenyl, naphthalene, diphenylether, tetralin, durene, prehnitene or 1,2,3,4-tetramethylbenzene, and the like. Preferably, excess hydroquinone and/or soluble acid catalyst are employed, in which case they also function as reaction medium.

Following alkylation, the intermediate product, cyclohexylhydroquinone (or derivative thereof), is recovered by conventional techniques, such as, for example, crystallization, extraction, distillation, precipitation and the like.

The dehydrogenation of the cyclohexylhydroquinone intermediate to produce the desired phenylhydroquinone product can be carried out under a wide variety of conditions; preferably in the presence of a dehydrogenation catalyst. It is expected that any catalyst (or reaction conditons) which is operable for the conversion of cyclohexane or cyclohexene to benzene will be suitable for use in the practice of the present invention, although it is recognized by those of skill in the art that other catalysts and/or reaction conditions will also be suitable. Examples of dehydrogenation catalysts useful in the practice of the present invention include Group 8 and Group 1B metals, as well as additional modifying components such as elemental sulfur, alkali metals and the early transition metals (i.e., Group IVA, V, VIA and VIIA metals). Presently preferred modifiers include sulfur and copper.

Especially preferred are dehydrogenation catalysts which promote minimum amounts of or essentially no hydrolysis of the hydroquinone hydroxy or alkoxy groups. Among the preferred catalysts are the noble metals. For ease of catalyst handling and to minimize catalyst expense, it is also preferred to use supported catalyst. A presently preferred catalyst support is carbon.

Expecially preferred catalysts are supported noble catalysts which have been treated with a modifying agent so as to minimize the occurrence of hydrogenolysis. Examples of presently preferred modifying agents include sulfur and copper. Examples of the presently preferred dehydrogenation catalysts for use in the practice of the present invention include sulfided palladium on alumina, sulfided palladium on carbon, sulfided platinum on carbon, palladium-copper on carbon support, and the like.

Reaction conditions for the dehydrogenation step can vary over a wide range, as can be readily determined by one of skill in the art. For example, a reaction temperature in the range of about 100° up to 500° C. is generally suitable, as is a reaction pressure in the range of about 0.01 up to 10 atmospheres, with contact times in the range of about 0.01 up to 36 hours. Preferred reaction parameters comprise a temperature in the range of about 225° up to 350° C., pressure in the range of 0.1 up to 1 atmosphere, and contact time in the range of about 0.01 up to 24 hours.

When dehydrogenation catalyst is employed, the dehydrogenation reaction can be conducted in either batch or continuous mode. When carried out in batch mode, the substrate to catalyst weight ratio employed typically falls within the range of about 10:1 up to 1000:1, with a substrate to catalyst weight ratio of about 20:1 up to 100:1 being preferred.

When carried out in continuous mode, the substrate to catalyst weight ratio will vary as a function of reactant space velocity, catalyst loading level, reactor design, and the like.

The use of solvent in the dehydrogenation step is optional. When employed, solvents which are stable under the dehydrogenation conditions are suitable, and are employed in amounts ranging from 10 up to 90 weight percent of the reaction mixture. Examples of suitable solvents include biphenyl, naphthalene, diphenylether, tetralin, durene, prehnitene or 1,2,3,4-tetramethylbenzene, and the like.

Those of skill in the art recognize that the catalyst utilized may be recycled from the slurry by filtering the hot reaction mixture. The filtration may be conducted at the reaction temperature, above the melting point of the reaction mixture or at a temperature between about 100° C. and 200° C. A preferred range of temperatures for recovering the catalyst by filtration is between about 125° C. and 150° C.

In a preferred embodiment of the invention, hydrogen gas produced as a result of the reaction is removed from the reaction atmosphere as the reaction proceeds. This can be accomplished by a variety of techniques as are well known by those of skill in the art. For example, the removal of hydrogen gas can be attained by circulating an inert gas through the atmosphere immediately above, or directly into, the reaction mixture. By means of example, the inert gas may be nitrogen. However, other unreactive gases may also be uitilized for the removal of the hydrogen gas. As one alternative, hydrogen gas can be removed by careful addition of a purge gas containing small amounts of a reactive gas, e.g., oxygen, which enables the removal of hydrogen as water.

The net result of hydrogen gas removal is to shift the equilibrium concentration from the starting material or substrate to the product of the reaction by removing from the system any amount of hydrogen produced.

In another preferred embodiment of the present invention, excellent product selectivities are obtained when small amounts (e.g., 0.5 up to 5 weight percent based on total weight of substrate) of biphenyl are present in the reaction mixture. The presence of biphenyl reduces the amount of undesired hydrogenolysis which occurs during the dehydrogenation step, thereby increasing selectivity to the desired products.

In accordance with yet another preferred embodiment of the present invention, the dehydrogenation reaction is carried out in the presence of small quantities of water in the reaction mixture. Water can be introduced into the reaction vessel in any suitable manner, such as for example, by subsurface addition, by passing over the reaction mixture as part of the inert gas purge, and the like. The quantity of water introduced into the reaction mixture is not believed to be critical, with a weight hourly space velocity (WHSV; i.e., rate) of water introduced as low as about 0.1 grams of water per gram of catalyst per hour providing the benefits of both improved selectivity and increased reaction rate. WHSV's up to about 100 g/g-hr are suitable, with a WHSV for water introduced in the range of about 0.1 up to 20 g/g-hr being preferred.

Following dehydrogenation, the desired phenylhydroquinone product can be recovered by conventional techniques, such as for example, by crystallization, extraction, distillation, precipitation and the like.

In a preferred embodiment of the present invention, the alkylation stage and the dehydrogenation stage can be integrated in such a fashion that by-product streams from the alkylation and dehydrogenation stages can be recovered and recycled for conversion to additional quantities of desired products. In this manner, di- and tri-substituted hydroquinone derivatives can be returned to the alkylation stage where they are disproportionated into additional quantities of the desired monoalkylated product. Similarly, unreacted cyclohexylhydroquinone and derivatives thereof can be recycled to the dehydrogenation stage and subjected to additional treatment under dehydrogenation conditions.

The invention will now be described in further detail by reference to the following non-limiting examples.

EXAMPLE 1

To a three-neck, one-liter, drop bottom vessel were added 96.4 g of 85% phosphoric acid and 72.3 g hydroquinone. The vessel and contents were heated to about 130° C., then 48.2 g of cyclohexanol was added as a steady stream over a period of one hour. Once cyclohexanol addition was complete, the reaction contents were maintained for an additional hour at 130° C., then cooled to 85° C. for workup.

Cyclohexylhydroquinone was extracted twice with 100 mL aliquots of toluene, and the acid layer retained for recycle. The combined toluene extracts were washed three times with 100 mL aliquots of water. A 77% yield of product of 99% purity was obtained after distillation at 170°–180° C. and a pressure of about 0.6 mm Hg.

100 g of cyclohexylhydroquinone (prepared as described in the previous paragraph) was contacted with 2 g of a 5% palladium on sulfided carbon catalyst in a three-neck, 250 mL round bottom flask equipped with a mechanical stirrer at 250° C. Residence time of the feed material in the reaction zone was about 24 hours.

Product was then recovered by cooling the dehydrogenation reaction mixture to about 100° C., adding a sufficient quantity of toluene (about 50 mL) to dissolve the phenylhydroquinone product, then filtering to remove catalyst. Product was then recrystallized from the toluene to give 88 g (90% yield) of >98% pure phenylhydroquinone.

The filtrate which remains after product recrystallization, and which consists primarily of toluene containing small amounts of phenylhydroquinone, cyclohexylhydroquinone, 2-phenylphenol and 3-phenylphenol, can be recycled back to be used for cyclohexylhydroquinone extraction following the alkylation reaction step.

EXAMPLE 2

A series of alkylation reactions were carried out in accordance with the procedure set forth in Example 1 employing a variety of acid catalysts. For the liquid acids (runs 1–5 of the Table), 96.4 g of acid were employed, with no added solvent. For the solid acids (runs 6 and 7 of the Table), about 7 g of solid acid catalyst (hydroquinone/acid weight ratio about 10/1) was employed, with about 15 g of xylene added as reaction diluent.

Workup was the same as described in Example 1 for the liquid acids, and simplified for the solid acids to involve filtration to remove catalyst, then crystallization of cyclohexylhydroquinone from the toluene-containing medium.

Reaction results are presented in Table 1.

TABLE 1

Alkylation of Hydroquinone with Cyclohexanol

| Run No. | Acid Catalyst | Isolated Yield CHQ*, % | Ratio of CHQ to DCHQ** |
|---|---|---|---|
| 1 | $H_3PO_4$ (85%) | 77 | 7/1 |
| 2 | $H_2SO_4$ (96%) | 62 | 5/1 |
| 3 | $CH_3SO_3H$ | 60 | 5/1 |
| 4 | $CF_3SO_3H$ | 55 | 4/1 |
| 5 | Polyphosphoric acid | 46 | 5/1 |
| 6 | Amberlyst 15 | 42 | 6/1 |
| 7 | $SiO_2/Al_2O_3$ | 40 | 7/1 |

*CHQ = cyclohexylhydroquinone
**DCHQ = dicyclohexylhydroquinone

These results demonstrate that a wide variety of acids can be employed for the alkylation of hydroquinone with cyclohexyl moieties such as cyclohexanol.

EXAMPLE 3

Dehydrogenation of Cyclohexylhydroquinone with a Variety of Dehydrogenation Catalysts A series of experiments were carried out to investigate the conversion of cyclohexylhydroquinone to phenylhydroquinone employing a variety of dehydrogenation catalysts. The experiments were all run at 250° C. in biphenyl as a solvent employing the procedure set forth below:

A 250-ml 3-neck flask was fitted with a tube for the subsurface addition of gas, a mechanical stirrer, a thermometer and a condenser.

A sample was prepared by adding to the flask 100 g biphenyl, 20 g cyclohexylhydroquinone and 2.0 g of catalyst, then the flask was heated to 250° C. During the course of the reaction, nitrogen gas was incorporated into the reaction atmosphere by subsurface addition thereof. After stirring the mixture for 24 hours at 250° C., an aliquot of the reaction mixture was analyzed by gas chromatography.

The results of the experiments are set forth in Table 2.

TABLE 2

Dehydrogenation of Cyclohexylhydroquinone Over a Variety of Dehydrogenation Catalysts

| Catalyst | Conversion (%) | Selectivity (%) |
|---|---|---|
| 5% Pd/carbon | 100 | 4 |
| 5% Pd/sulfided carbon | 78 | 95 |
| 5% Pt/carbon | 99 | 20 |
| 5% Pt/sulfided carbon | 65 | 90 |
| 8% Pd, 2% Pt/carbon | 95 | 42 |
| 5% Rh/carbon | 37 | 69 |
| 5% Pd, 1.5% Cu/carbon | 88 | 90 |
| 5% Pd, 0.8% Ag/carbon | 72 | 57 |
| 5% Pd, 2.5% Cu/$Al_2O_3$ | 20 | 65 |
| 5% Pd, 2.5% Cu/$SiO_2$ | 12 | 82 |
| 5% Pd, 2.5% Cu/carbon | 43 | 99 |

All catalysts tested give high levels of cyclohexylhydroquinone conversion, or good selectivities to the desired product, phenylhydroquinone, or both.

EXAMPLE 4

Dehydrogenation of cyclohexylhydroquinone was carried out in the absence and presence of biphenyl to demonstrate the effect of the presence of small amounts of biphenyl on product selectivity. The dehydrogenation was carried out as described in Example 1, with the results set forth in Table 3.

TABLE 3

Effect of Biphenyl on Dehydrogenation of Cyclohexylhydroquinone

| Catalyst | Additive* | Conversion, % | Selectivity, % |
|---|---|---|---|
| 5% Pd on Sulfided Carbon | None | 95 | 82 |
| 5% Pd on Sulfided Carbon | 1 wt % | 95 | 95 |

*Biphenyl loading wt % based on total weight of substrate

These results demonstrate that the presence of small amounts of biphenyl in the dehydrogenation reaction mixture promotes the formation of phenylhydroquinone with very high selectivity.

EXAMPLE 5

Dehydrogenation of cyclohexylhydroquinone was carried out in the absence and presence of water to demonstrate the effect of the presence of small amounts of water on catalyst activity and product selectivity. The dehydrogenation was carried out by contacting 100 g of cyclohexylhydroquinone with 2 g of a 5% palladium on sulfided carbon catalyst at 250° C. in a three-neck, 250 mL round bottom flask equipped with a mechanical stirrer. An aliquot of 5 grams of water (WHSV=2.5) was introduced into the reaction medium via subsurface injection each hour. The results are set forth in Table 4.

TABLE 4

Effect of Water on Dehydrogenation of Cyclohexylhydroquinone

| Catalyst | Additive | Conversion, % | Selectivity, % |
|---|---|---|---|
| 5% Pd on Sulfided Carbon | None | 58 (6 hrs) 95 (24 hrs) | 91 82 |
| 5% Pd on Sulfided Carbon | Water, WHSV 2.5 | 95 (6 hrs) | 91 |

These results demonstrate that the presence of small amounts of water in the dehydrogenation reaction mixture promotes the formation of phenylhydroquinone with very high selectivity at substantially improved reaction rates relative to reaction in the absence of added water.

The invention has been described in detail with reference to particular embodiments thereof. It will be understood, however, that variations and modifications can be effected within the spirit and scope of the invention.

We claim:

1. A process for the preparation of phenylhydroquinone derivatives of the structure

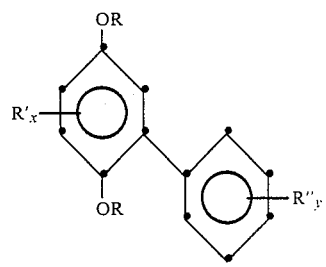

wherein:

each R is independently H, a $C_1$–$C_{20}$ alkyl or substituted alkyl radical;

wherein Y is a $C_1$–$C_{20}$ alkyl or substituted alkyl radical; or a $C_6$–$C_{12}$ aryl, alkyl substituted aryl or substituted aryl radical;

each R' is independently a $C_1$–$C_{20}$ alkyl or substituted alkyl radical; a $C_5$–$C_{12}$ cycloalkyl or substituted cycloalkyl radical;

wherein Y is a $C_1$–$C_{20}$ alkyl or substituted alkyl radical; or a $C_6$–$C_{12}$ aryl, alkyl substituted aryl or substituted aryl radical;

wherein R'' is the same as R', and each R'' is selected independently of R' and independently of one another;

wherein the substituents, when present on R, R' or R'' are selected from the group consisting of:

—OR, wherein R is as defined above;

—$NO_2$;

—X, wherein X is a halide;

wherein R is as defined above;

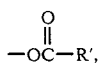

wherein R' is as defined above; and

—$SO_zR$, wherein z is an integer which varies in the range of 0 up to 3 and R is as defined above;

wherein x is a whole number in the range of 0 up to 3; and wherein y is a whole number in the range of 0 up to 5;

said process comprising:

(1) contacting a hydroquinone compound of the structure:

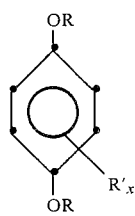

with a cyclic compound of the structure:

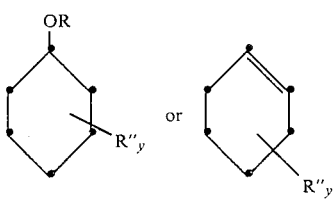

in the presence of an acid under alkylation conditions suitable to produce a cyclohexylhydroquinone of the structure:

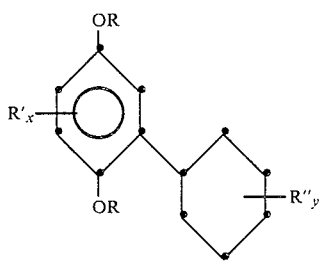

and thereafter (2) subjecting said cyclohexylhydroquinone to dehydrogenation conditions which minimize the occurrence of hydrogenolysis.

2. A process in accordance with claim 1 wherein said acid is selected from the group consisting of:
phosphoric acid,
sulfuric acid,
methanesulfonic acid,
trifluoromethanesulfonic acid,
polyphosphoric acid,
acidic molecular sieves,
$SiO_2/Al_2O_3$,
p-toluenesulfonic acid,
trichloroacetic acid,
dichloroacetic acid,
trifluoroacetic acid,
aluminum trichloride,
aluminum tribromide,
boron trifluoride, and
acidic polymeric resins, such as, for example, Amberlyst 15, and Aerocat.

3. A process in accordance with claim 2 wherein said acidic polymeric resin is selected from the group consisting of:
Amberlyst 15, and
Aerocat.

4. A process in accordance with claim 1 wherein said acid is phosphoric acid.

5. A process in accordance with claim 2 wherein said alkylation conditions comprise a temperature in the range of about 0° up to 200° C., pressure in the range of 0.01 up to 10 atm, and a contact time in the range of 0.01 up to 36 hours.

6. A process in accordance with claim 1 wherein said alkylation is carried out in continuous fashion.

7. A process in accordance with claim 1 wherein said dehydrogenation is carried out in the presence of a dehydrogenation catalyst.

8. A process in accordance with claim 7 wherein said dehydrogenation catalyst is selected from the group consisting of any one of the elements selected from Group VIII and Group IB.

9. A process in accordance with claim 8 wherein said dehydrogenation conditions comprise a temperature in the range of 100° up to 500° C., a reaction pressure in the range of 0.01 up to 1 atm, and a contact time in the range of 0.01 up to 36 hours.

10. A process in accordance with claim 8 wherein said dehydrogenation catalyst is deposited on a support.

11. A process in accordance with claim 10 wherein said support is carbon.

12. A process in accordance with claim 8 wherein said dehydrogenation catalyst is selected from the group consisting of any one of the Noble metals.

13. A process in accordance with claim 8 wherein said catalyst further comprises a modifier.

14. A process in accordance with claim 13 wherein said modifier is selected from the group consisting of sulfur and copper.

15. A process in accordance with claim 7 wherein said dehydrogenation is carried out in continuous fashion.

16. A process in accordance with claim 7 wherein said dehydrogenation is carried out in the presence of water.

17. A process in accordance with claim 16 wherein water is introduced at a rate in the range of 0.1 up to 100 grams water per gram catalyst per hour.

18. A process in accordance with claim 7 wherein said dehydrogenation is carried out in the presence of about 0.5 up to 5.0 wt % of biphenyl, based on the total weight of substrate.

19. A process in accordance with claim 9 wherein said catalyst is selected from the group consisting of:
Pd-Cu/C,
Pd on sulfided carbon, and
Pt on sulfided carbon.

20. A process in accordance with claim 1 wherein R is selected from the group consisting of:
—H,
—CH₃,
—C₆H₅, and

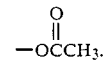

21. A process in accordance with claim 1 wherein R is H.

22. A process in accordance with claim 1 wherein x=y=0.

23. A process in accordance with claim 1 wherein R' is selected from the group consisting of:
2-Cl
2-CH₃,
2-cyclohexyl
2-isopropyl,
2-t-butyl, 2-octyl,
2-dodecyl,
2-octadecyl,
2-butanoyl,
2-octanoyl,
2-dodecanoyl, and
2-octadecanoyl.

24. A process in accordance with claim 1 wherein R" is 4-CH$_3$.

25. A process in accordance with claim 1 wherein the poly-alkylated by-products are recycled to the alkylation reaction for disproportionation into additional quantities of mono-alkylated product.

26. A process in accordance with claim 1 wherein unreacted cyclohexylhydroquinone is recycled to the dehydrogenation reaction for conversion into additional quantities of phenylhydroquinone.

* * * * *